United States Patent
Norris

(10) Patent No.: US 9,930,918 B2
(45) Date of Patent: Apr. 3, 2018

(54) HANDS-FREE SUCTIONING DEVICE

(71) Applicant: Sanverbos, Inc., Sonoma, CA (US)

(72) Inventor: Sean Norris, Sonoma, CA (US)

(73) Assignee: Sanverbos, Sonoma, CA (US)

( * ) Notice: Subject to any disclaimer, the term of this patent is extended or adjusted under 35 U.S.C. 154(b) by 357 days.

(21) Appl. No.: 14/837,171

(22) Filed: Aug. 27, 2015

(65) Prior Publication Data

US 2016/0073712 A1   Mar. 17, 2016

Related U.S. Application Data

(60) Provisional application No. 62/049,617, filed on Sep. 12, 2014.

(51) Int. Cl.
| | | |
|---|---|---|
| *A41D 19/00* | (2006.01) | |
| *A61C 17/06* | (2006.01) | |
| *A61D 19/04* | (2006.01) | |

(52) U.S. Cl.
CPC ........ *A41D 19/0079* (2013.01); *A61C 17/043* (2013.01); *A61D 19/04* (2013.01)

(58) Field of Classification Search
CPC ...... A61B 19/04; A41D 19/00; A41D 19/002; A42D 19/02
See application file for complete search history.

(56) References Cited

U.S. PATENT DOCUMENTS

| | | | | | |
|---|---|---|---|---|---|
| 4,766,914 | A | * | 8/1988 | Briggs | A45D 20/00 132/212 |
| 5,728,516 | A | * | 3/1998 | Edwards | G03C 1/035 430/567 |
| 7,391,648 | B2 | * | 6/2008 | Pekny | G11C 5/145 365/185.2 |
| 2007/0192931 | A1 | | 8/2007 | Schneider | |
| 2011/0046544 | A1 | * | 2/2011 | Beeley | A61B 42/10 604/23 |

FOREIGN PATENT DOCUMENTS

GB     2307850 A  *  6/1997  ............... A47L 5/24

* cited by examiner

*Primary Examiner* — Tejash Patel
(74) *Attorney, Agent, or Firm* — Stamoulis & Weinblatt LLC

(57) ABSTRACT

Medical gloves are disclosed with one or more channels running from a cuff of the glove to the tip of one or more fingers. The channel may extend at least partially around the fingertip and may comprise a one or more orifices positioned at least partially around the fingertip. A suction source may be coupled to the channel to provide suction at the orifices.

38 Claims, 12 Drawing Sheets

HANDS-FREE SUCTIONING DEVICE

CROSS-REFERENCE TO RELATED APPLICATIONS

The present application claims the benefit of U.S. Provisional Application No. 62/049,617, filed on Sep. 12, 2014, the entire disclosure of which is hereby incorporated by reference for all purposes.

FIELD OF THE INVENTION

The present technology relates generally to medical devices used in at least the medical, dental, and veterinary environments, and, more particularly, to a medical glove with an incorporated suction device.

BACKGROUND OF THE DISCLOSURE

Medical gloves, which include both surgical and patient examination gloves, are used to prevent transmission of a wide variety of diseases, such as bacterial or viral infections, to both patients and health care personnel such as surgeons, dentists, veterinarians, and health care workers. While patient examination gloves are intended to prevent contamination between the patient and the examiner, surgical gloves are worn by operating room personnel to protect a surgical wound from contamination.

Additionally, during dental or medical procedures, suctioning devices are used to remove fluids, such as saliva, vomit, or blood, from the area being operated on to allow surgeons to view and work on the area, or debris such as tissue, bone, or amalgam. For example, in some dentistry procedures such as cavity fillings, it is important that the tooth stay clean and dry, so the suction removes any saliva, blood, and water from dental drills that accumulate around the tooth.

Often times when suction is used during dental or medical procedures, the operating surgeon or dentist must hold the suction himself or an assistant must be present to perform the suctioning. However, it is desirable for the operating surgeon's or dentist's hands to be free to perform other important tasks while still maintaining the ability to suction. Additionally, current suction instruments are imprecise extensions of the operating surgeon's or dentist's hand in comparison to the operating surgeon's or dentist's own fingers which are controlled, precise, dexterous, and flexible.

Embodiments of the present disclosure are directed to a medical glove with an incorporated suction device. A medical glove with a suction device incorporated within the material of the medical glove along the index or multiple fingers will allow the operating surgeon or dentist the use of both hands and the ability to suction during a procedure while retaining flexibility for dexterity and precise manipulation at his fingers.

SUMMARY

The present application is directed to medical gloves. An exemplary glove may comprise a cuff having an opening for hand entry and opening edge. The glove may further comprise a body section coupled to the cuff and a plurality of finger members coupled to the body section generally opposite from the cuff. Each finger member may comprise a base end where the finger member is coupled to be body section and a tip end opposite the base end. A channel may be integrally formed in the glove, and may comprise a first open end proximate to the opening edge and a second open end proximate to the tip end of one of the finger members. An enclosed hollow space may connect the first open end and the second open end.

According to additional exemplary embodiments, the present application may be directed to medical gloves. An exemplary glove may comprise a cuff having an opening for hand entry and opening edge. The glove may further comprise a body section coupled to the cuff and a plurality of finger members coupled to the body section generally opposite from the cuff. Each finger member may comprise a base end where the finger member is coupled to be body section and a tip end opposite the base end. A channel may be integrally formed in the glove, and may comprise a first open end proximate to the opening edge and a second open end proximate to the tip end of one of the finger members. The second open end may comprise a plurality of orifices dispersed radially around at least a portion of the tip end of the finger member. An enclosed hollow space may connect the first open end and the second open end.

According to further exemplary embodiments, the present application may be directed to medical gloves. An exemplary glove may comprise a cuff having an opening for hand entry and opening edge. The glove may further comprise a body section coupled to the cuff and a plurality of finger members coupled to the body section generally opposite from the cuff. Each finger member may comprise a base end where the finger member is coupled to be body section and a tip end opposite the base end. A channel may be integrally formed in the glove, and may comprise a first open end proximate to the opening edge and a second open end proximate to the tip end of one of the finger members. An enclosed hollow space may connect the first open end and the second open end. A support member may be positioned within the channel and may extend along at least a portion of a length of the channel. The support member may have a generally hollow interior to allow the passage of liquids and gases through the channel.

According to still further exemplary embodiments, the present application may be directed to medical gloves. An exemplary glove may comprise a cuff having an opening for hand entry and opening edge. The glove may further comprise a body section coupled to the cuff and a plurality of finger members coupled to the body section generally opposite from the cuff. Each finger member may comprise a base end where the finger member is coupled to be body section and a tip end opposite the base end. A channel may be integrally formed in the glove, and may comprise a first open end proximate to the opening edge and a second open end proximate to the tip end of one of the finger members. An enclosed hollow space may connect the first open end and the second open end. A suction head may be inserted into the second open end. The suction head may comprise a nipple that is at least partially inserted in the channel through the second open end, and a suction head extending outside the channel and generally conforming to a rounded shape of the tip end of the finger member. A plurality of orifices may be dispersed along the suction head.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Figure 1:
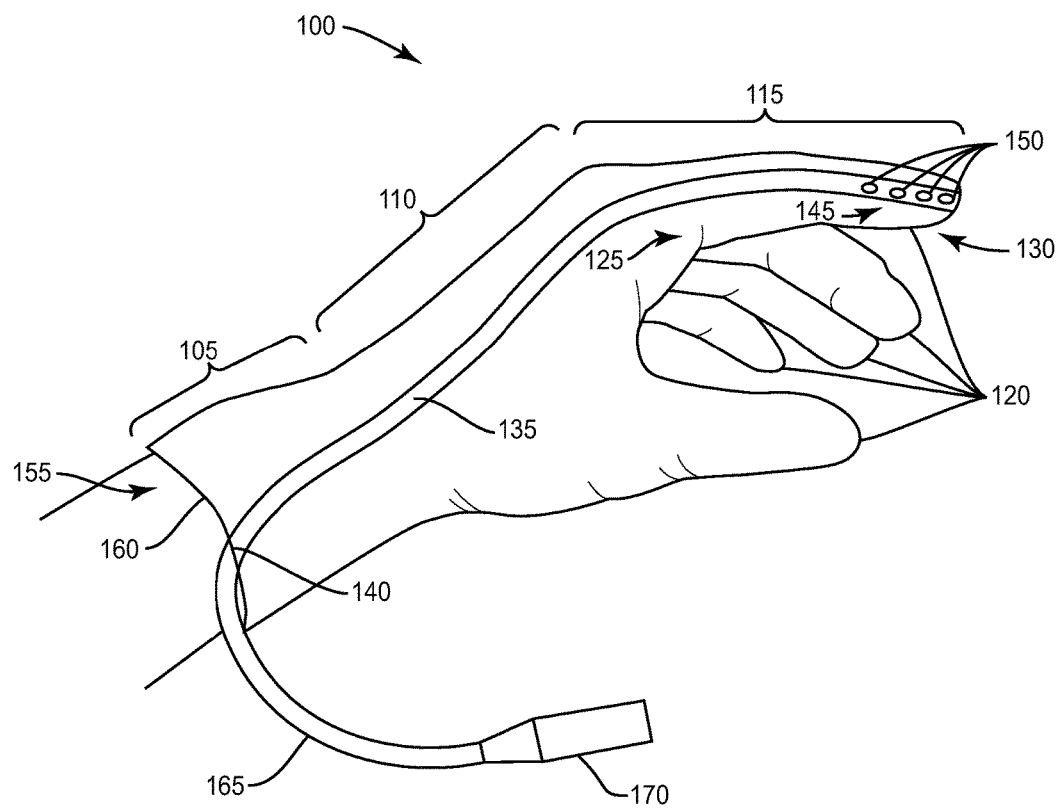
FIG. 1 illustrates a side view of a medical glove with an integrated channel according to various embodiments.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the technology. As used herein, the singular forms "a", "an" and "the" are intended to include the plural forms as well, unless the context clearly indicates otherwise.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

Embodiments of the present invention are directed to a medical glove with an incorporated suction device.

FIG. 1 illustrates an exemplary embodiment of a medical glove 100, comprising a cuff 105, a body section 110 coupled to the cuff 105, and a finger section 115. The cuff 105 may further comprise an opening 155 for hand entry, the opening 155 having an opening edge 160. The finger section 115 may comprise a plurality of individual finger members 120. Each finger member 120 comprises a base end 125 where the finger member 120 couples to the body section 110, and a tip end 130 opposite the base end 125. The body section 110 of the medical glove 100 may couple the cuff 105 and the finger section 115 and may generally cover a top of a hand and a palm of a user of the medical glove 100. The medical glove 100 may further comprise an enclosed hollow channel 135 beginning at a first open end 140 proximate to the cuff opening edge 160, extending continuously across the cuff 140, body section 110 and at least one finger member 120. The channel 135 may terminate at a second open end 145 proximate to the tip end 130 of the finger member 120. In various embodiments, the medical glove 100 may further comprise a suction tubing 165 within the channel 135 (see FIG. 12). The tubing 165 may extend beyond the cuff opening edge 160 as illustrated in FIG. 1 and terminate at a connector 170 to facilitate connection to a suction source.

In various embodiments, the medical glove 100 may be made out of synthetic or non-synthetic polymers such as latex, vinyl, nitrile, polyurethane, and the like. Furthermore, the medical gloves 100 may be disposable, reusable, sterile, or not sterile for non-surgical uses. In various embodiments in which suction tubing 165 is incorporated within the material of medical glove 100, there is no separation between suction tubing 165 and the surrounding glove material. If a perforation is encountered in the medical glove 100 around suction tubing 165, an indicator glove underneath (not shown) may show any possible leakage.

Figure 2:
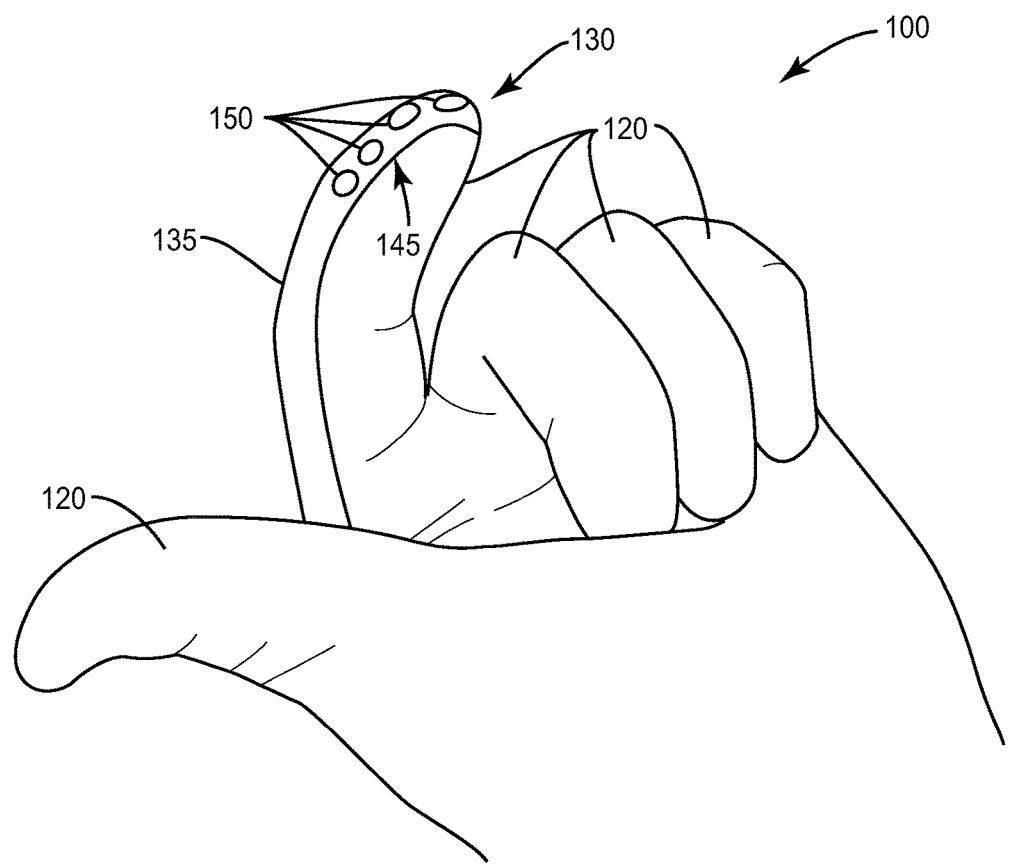
FIG. 2 illustrates a front view of a medical glove with an integrated channel according to various embodiments.
Figure 3:
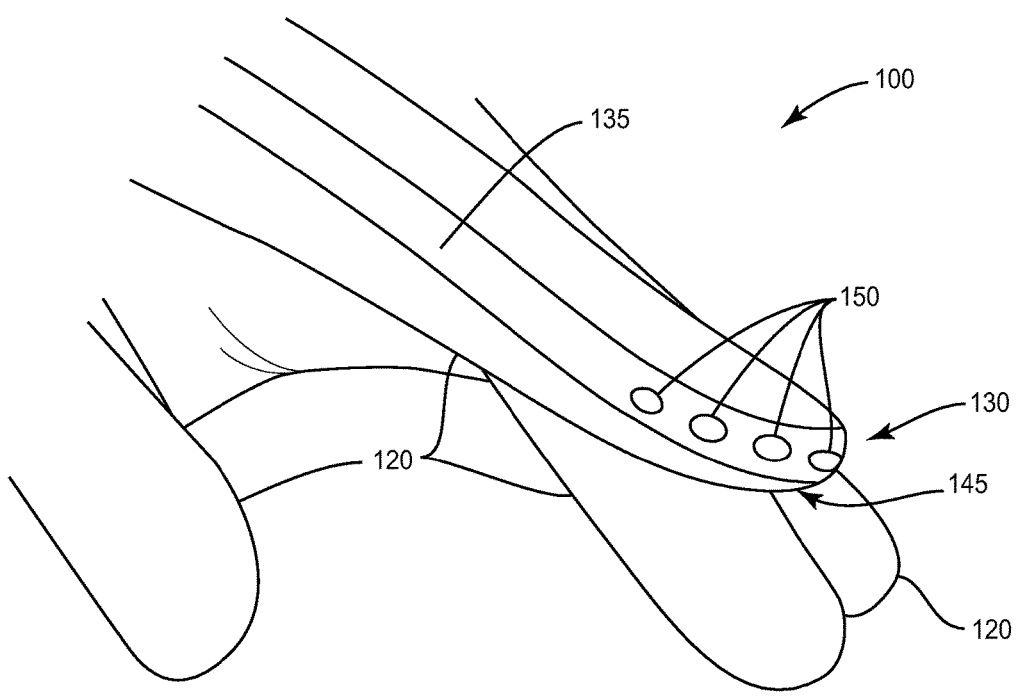
FIG. 3 illustrates a side view of finger members of a medical glove with an integrated channel according to various embodiments.

FIGS. 2 and 3 illustrates the second open end 145 of the channel 135 at the tip end 130 of the finger member 120, according to various embodiments in which the second open end 145 comprises a plurality of individual orifices 150. Although certain embodiments may comprise a single orifice 150, having a plurality of orifices 150 may better facilitate the second open end 145 to function as a pool suction device, thereby allowing suctioning of large volumes of fluid. Further, distributing the plurality of orifices 150 along a side of the fingertip 130 and at least partially around the fingertip 130 allows the user to easily position one or more of the orifices 150 precisely and accurately where needed with less overall movement of the user's finger. The plurality of orifices 150 may allow for continuous suction without clogging. In various embodiments, the orifices 150 may be any shape, size, or in any position at the tip end 130 of the finger member 120 that allows for continuous suction without clogging. For example, a dentist utilizing the medical glove 100 could maneuver his finger to suction an area accumulating saliva or dry the area around a tooth during an examination or procedure. Additionally, a general surgeon, for example, utilizing the medical glove 100 could maneuver his finger into a difficult to reach or non-visible area to suction blood or fluid from the obstructed surgical field.

Figure 4:
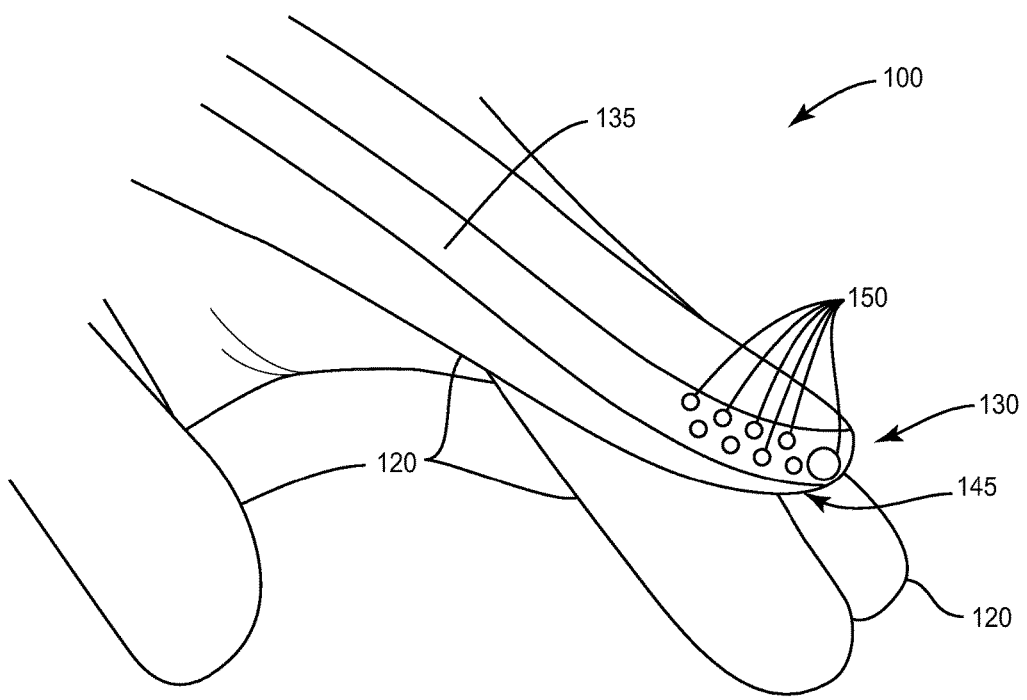
FIG. 4 illustrates a side view of finger members of a medical glove with an integrated channel according to various embodiments.
Figure 5:
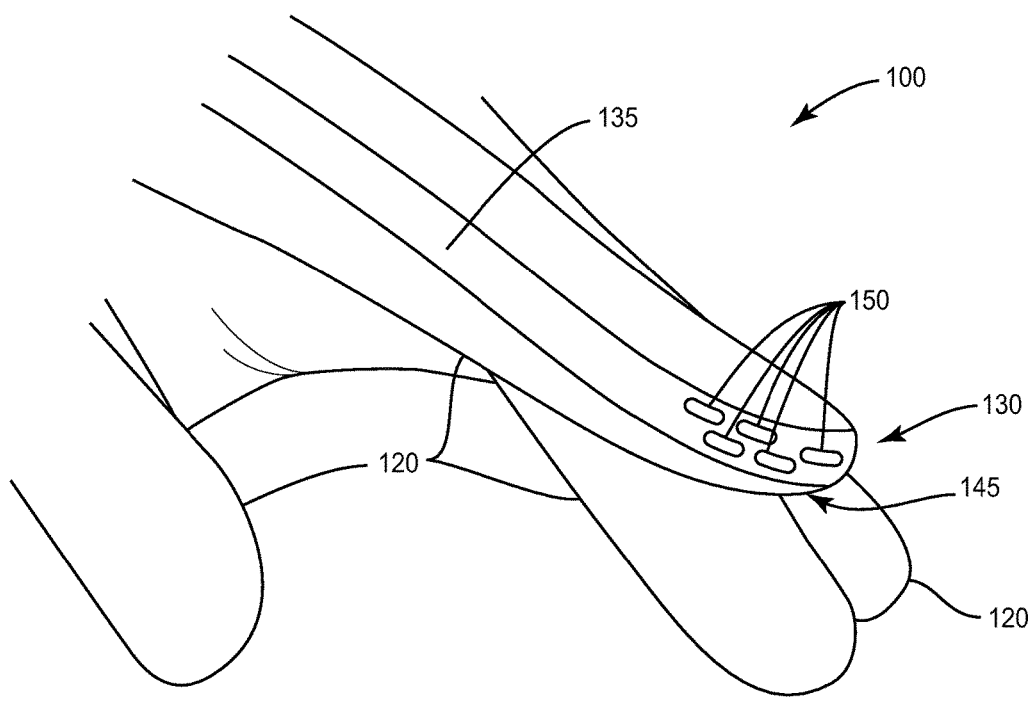
FIG. 5 illustrates a side view of finger members of a medical glove with an integrated channel according to various embodiments.
Figure 6:
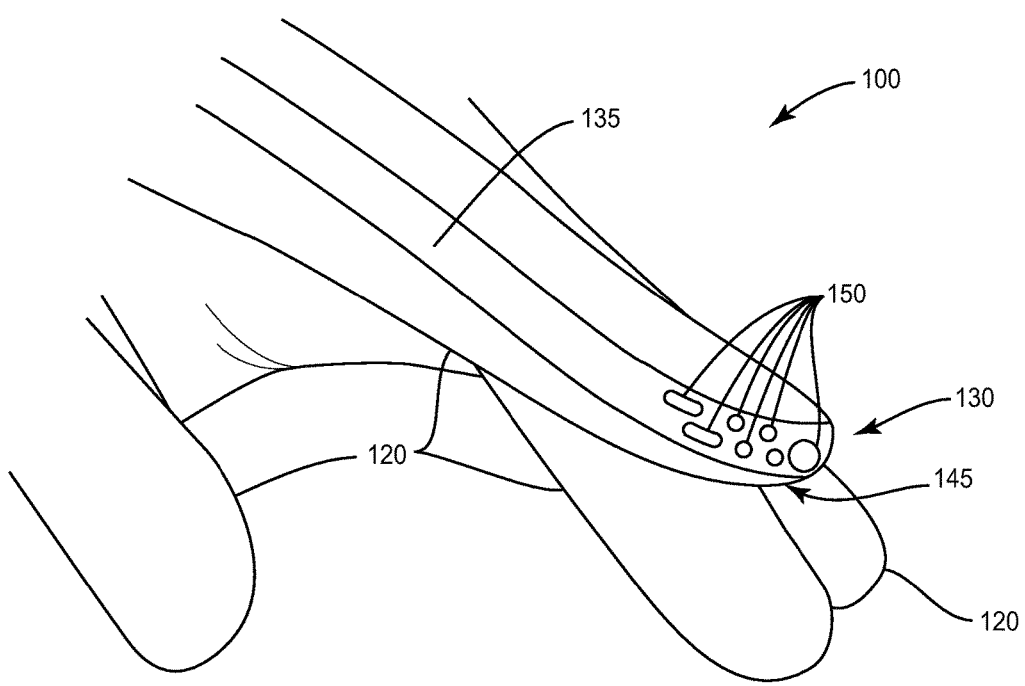
FIG. 6 illustrates a side view of finger members of a medical glove with an integrated channel according to various embodiments.

As mentioned above, the plurality of orifices 150 may be any shape or size, and may be located in any position in proximity to the tip end 130 of the finger member 120. FIGS. 4 through 6 illustrate certain nonlimiting examples of shape, size and positioning of a variety of orifices 150. Although FIGS. 1 through 3 illustrated a single row of generally equally sized orifices 150, FIG. 4 illustrates that various embodiments may comprise multiple rows and sizes of orifices 150 in combination. In the example of FIG. 4, a single larger orifice 150 may be positioned in close proximity to the tip end 130. The larger orifice 150 may be useful in, for example, dental applications where solid material may need to be suctioned away but which may clog smaller orifices 150. The smaller orifices 150 in FIG. 4 may be used to suction away liquids. In FIG. 5, the orifices 150 comprise slots instead of generally round holes to further facilitate removal of solids or to facilitate the removal of larger volumes of liquid in a shorter period of time. FIGS. 4 and 5 also illustrated that multiple rows of orifices 150 may be combined with a single row of orifices 150. In further exemplary embodiments as illustrated in FIG. 6, a variety of shapes, sizes, and rows of orifices 150 may be used in combination. Thus, as will be clear to one skilled in the art from the various embodiments illustrated in FIGS. 1-6, any shape, size, orientation, or combination of orifices 150 is within the scope of the present disclosure.

Figure 7:
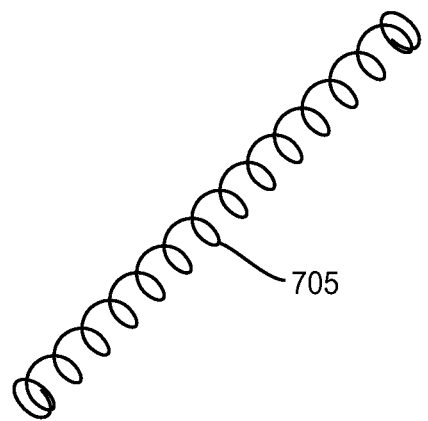
FIG. 7 illustrates a support member according to various embodiments.
Figure 8:
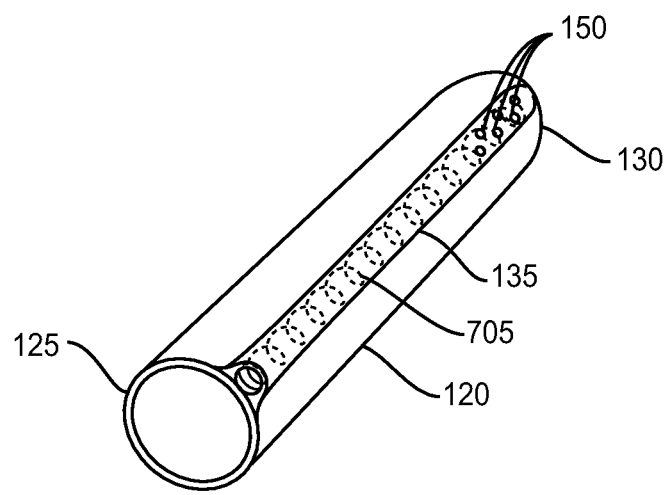
FIG. 8 illustrates a support member positioned in a channel on a finger member of a medical glove according to various embodiments.

Placing the channel 135 under suction may have a tendency to cause the channel 135 to at least partially collapse, thereby limiting the suctioning capability of the medical glove 100. FIG. 7 illustrates a reinforcing coil 705 that may be molded into sidewalls of the channel 135, or may be inserted into the channel 135. The coil 705 may comprise a flexible yet resilient material such as an elastomeric or other polymeric material to retain flexibility for dexterity and precise manipulation of the user's fingers. In certain embodiments, the coil 705 may comprise a metal, such as stainless steel or titanium. Additionally, the coil 705 may be of any length desired, and may run the entire length of the channel 135 or any portion or portions of the channel 135. In various embodiments, the coil 705 may be absent where finger joints of the user would be located to further aid in finger flexibility. FIG. 8 illustrates various embodiments in which the coil 705 is positioned in the channel 135 along the length of the finger member 120 from the base end 125 to the location of the orifices 150.

Figure 9:
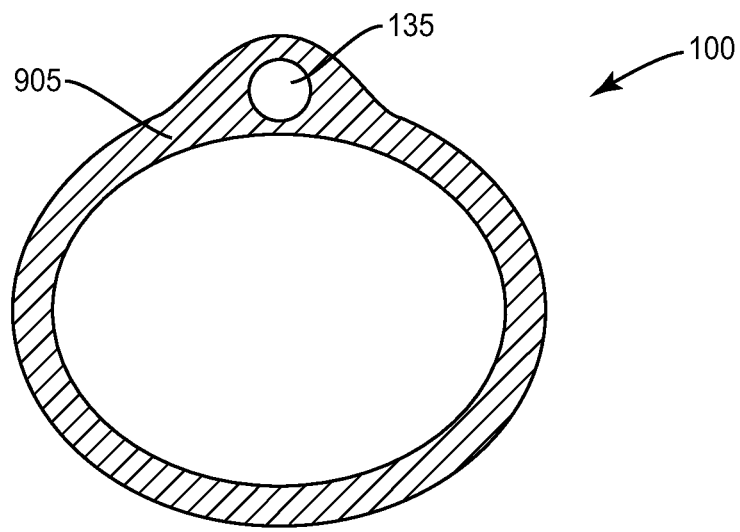
FIG. 9 illustrates a cross-sectional view of a medical glove with an integrated channel according to various embodiments.
Figure 10:
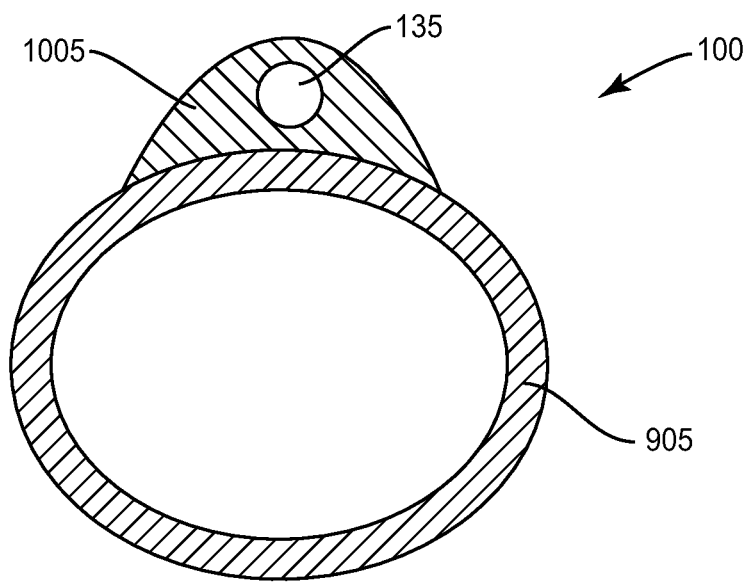
FIG. 10 illustrates a cross-sectional view of a medical glove with an integrated channel according to various embodiments.

FIGS. 9-12 illustrate cross-sectional views of the medical glove 100 that may be taken at any position along a length of the medical glove 100. FIG. 9 illustrates various embodiments in which the entire medical glove 100, including the portion comprising the channel 135, comprises a single material 905. The material 905 may be any material known in the art now or in the future for manufacturing medical gloves 100, such as latex, nitrile rubber, vinyl, neoprene, and the like. The channel 135 may be molded into the medical glove 100 as part of the manufacturing process. FIG. 10 illustrates various embodiments in which the medical glove 100 comprises a first material 905, and a portion of the medical glove 100 comprising the channel 135 comprises a second material 1005. The second material 1005 may be a more resilient composition than that of the first material 905 to provide additional structural strength to the sidewalls of the channel 135 such that the channel better resists collapsing when subjected to vacuum. The resilient second material 1005 may obviate the need to a reinforcing coil 705. Nonlimiting examples of the second material 1005 include polyisoprene or other resilient rubber compounds, silicone or other silicone-containing compounds, a fiber reinforced compound, a thermosetting polymer, or the like.

Figure 11:
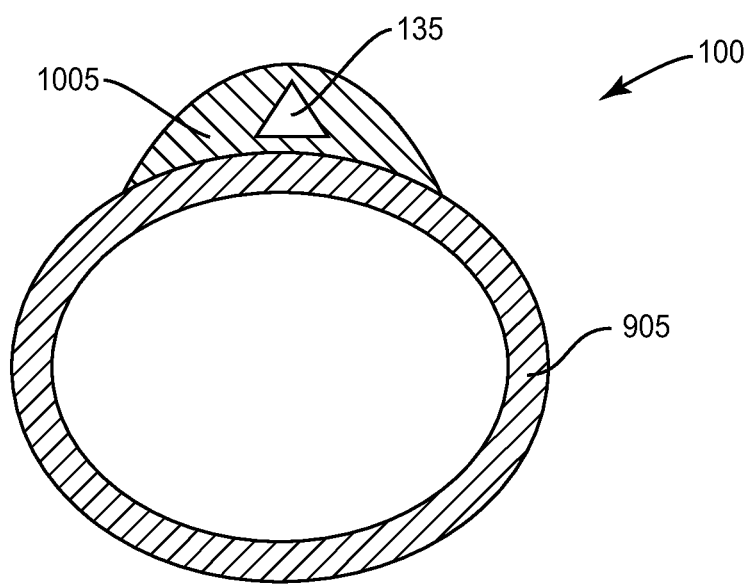
FIG. 11 illustrates a cross-sectional view of a medical glove with an integrated channel according to various embodiments.

In the previous figures, the channel 135 is depicted as being generally round or oval. The scope of the present disclosure includes any shape channel 135 known in the art. For example, FIG. 11 illustrates various embodiments of a triangular shaped channel 135 formed in the second material 1005. The triangular shape, as well as other shapes not shown, may provide higher structural strength to resist sidewall collapse when the channel 135 is under suction. Different shapes of the channel 135 may also be advantageous for easier formation of the channel 135 during manufacture of the medical glove 100.

Figure 12:
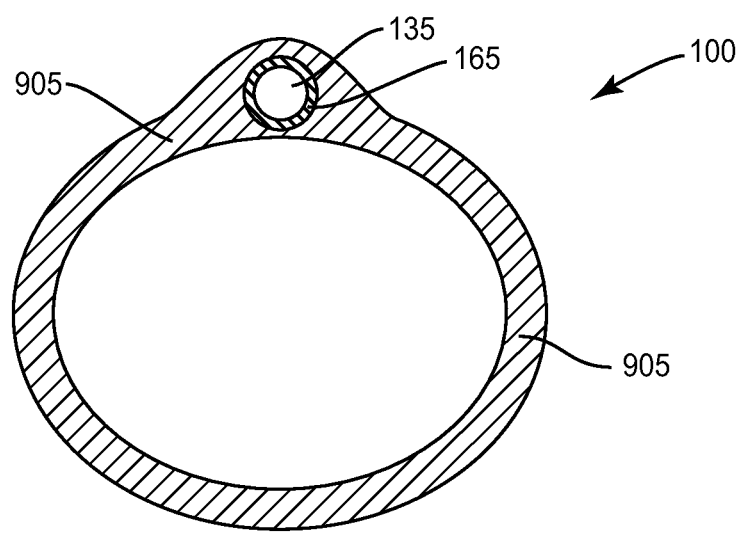
FIG. 12 illustrates a cross-sectional view of a medical glove with an integrated channel according to various embodiments.

FIG. 12 illustrates suction tubing 165 imbedded with the glove material 905 (or the second material 1005) to form the channel 135. As illustrated previously in FIG. 1, the suction tubing 165 may extend beyond the cuff opening edge 160 and terminate at the connector 170 to facilitate connection to a suction source. The suction tubing 165 may extend from the cuff opening edge 160 up to (and including in certain embodiments) the orifices 150, or any portion of that length.

Figure 13:
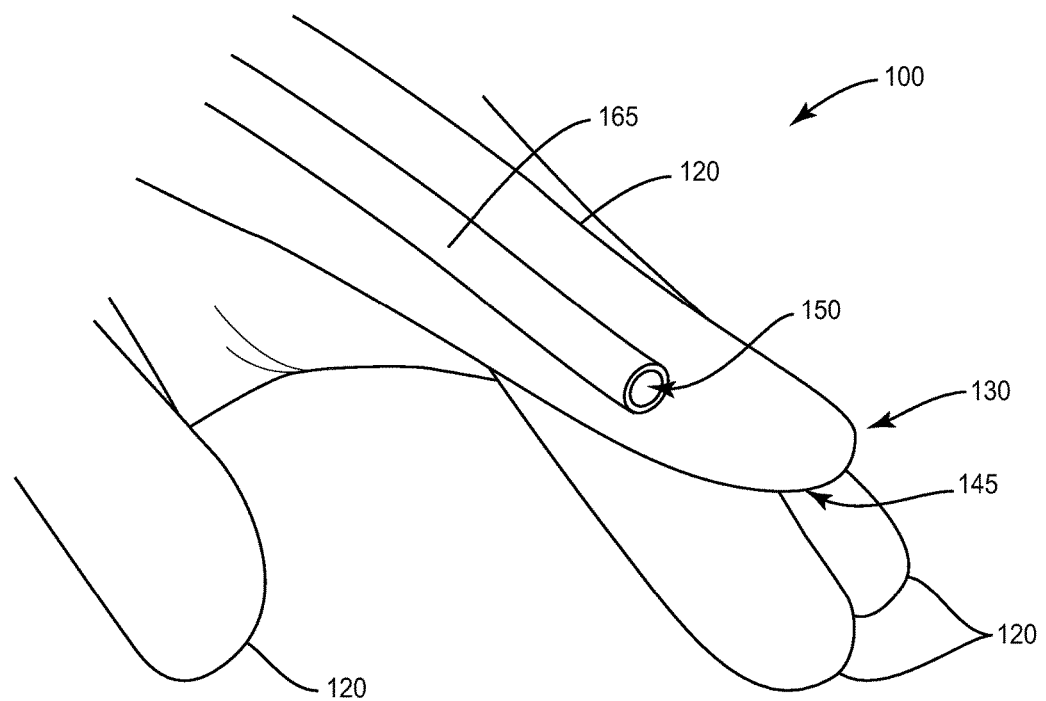
FIG. 13 illustrates a side view of finger members of a medical glove with an integrated channel according to various embodiments.

In certain situations, it may be advantageous to terminate the channel 165 before the tip end 130 of the finger member 120 as illustrated in FIG. 13 according to various embodiments. For example, the channel 165 may provide irrigation rather than suction, and placement of the source of the irrigation close to the tip end 130 may not be critical. In the example of FIG. 13, the channel 165 may terminate at a single orifice 150 designed to facilitate a flow of saline solution or other liquid.

Figure 14:
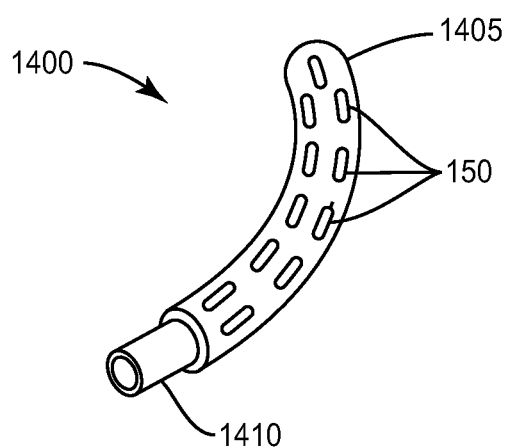
FIG. 14 illustrates a perspective view of a suction head according to various embodiments.
Figure 15:
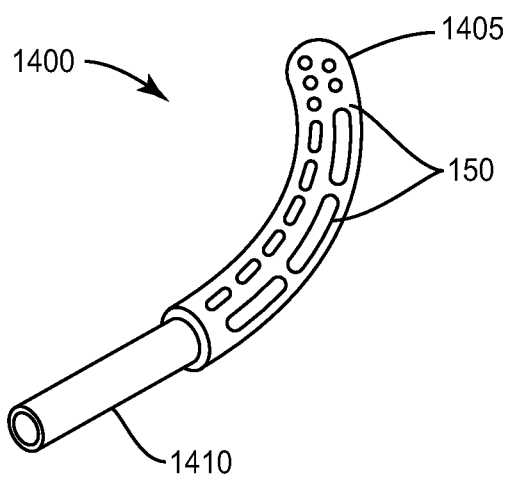
FIG. 15 illustrates a perspective view of a suction head according to various embodiments.

The embodiments illustrated in FIG. 13 may also facilitate the use of insertable suction tips 1400 as shown in FIGS. 14 and 15. The suction tips 1400 may comprise a suction head 1405 having one or more orifices 150, and a nipple 1410 adapted for releasable insertion into the channel 165 (such as the embodiment illustrated in FIG. 13). The nipple 1410 may be short as illustrated in FIG. 14 or longer as illustrated in FIG. 15 as is needed for specific applications. The insertable suction tips 1400 allow the user to select the proper orientation, location, and size of orifices 150 for the specific application. For example, a dentist may initially choose the insertable suction tip 1400 shown in FIG. 14 with small orifices 150. During the procedure, the dentist may encounter more solid material to be suctioned away than originally anticipated, which may cause repeated clogging of the orifices 150. In this situation, the dentist may remove the first insertable suction tip 1400 and replace it with the insertable suction tip 1400 shown in FIG. 15 that has larger orifices 150 designed to handle increased amounts of solids. Additionally, the dentist may remove the first insertable suction tip 1400 to quickly clean out debris clogged in orifices 150 and may reattach the first insertable suction tip 1400 without needing to remove or replace the medical glove 100.

Although FIGS. 14 and 15 illustrate that the insertable suction tip 1400 is curved to conform to the tip end 130 of the finger member 120, any desired shape is within the scope of the present disclosure.

Figure 16:
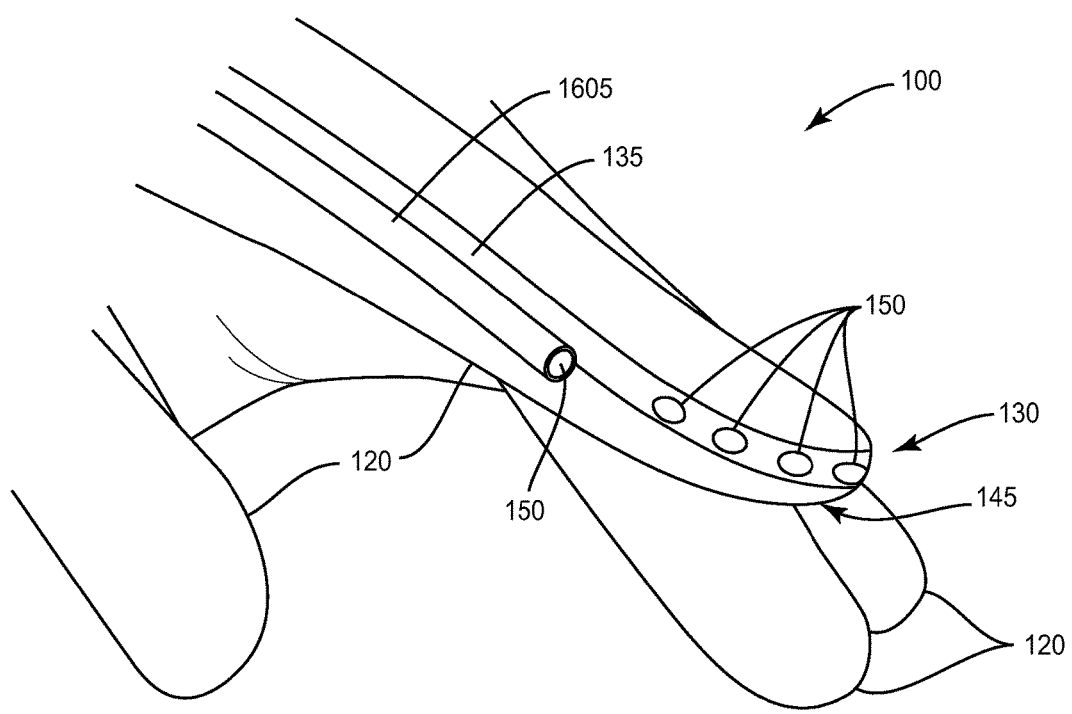
FIG. 16 illustrates a side view of finger members of a medical glove with a first integrated channel and a second integrated channel according to various embodiments.

The previous figures have illustrated a single channel 135 running from the cuff opening edge 160 to a single finger member 120. FIG. 16 illustrates various embodiments comprising a second channel 1605. The second channel 1605 may, for example, provide an irrigation source while the first channel 135 provides suction. Alternatively, the second channel 1605 may provide a second suction source. The second channel 1605, if used as a second suction source, may join with the first channel 135 at any point along the cuff 105, body section 110, or finger section 115. Alternatively, the second channel 1605 may be entirely separate from the first channel 135, terminating at the cuff opening edge 160. Any number of common or separate channels, 135, 1605 directed to any or all of the finger members 120 on either a left-handed or right-handed medical glove 100 are understood to be within the scope of the present disclosure, regardless of how arranged on the medical glove 100.

While the present technology has been described in connection with a series of preferred embodiments, these descriptions are not intended to limit the scope of the technology to the particular forms set forth herein. It will be further understood that the methods of the technology are not necessarily limited to the discrete steps or the order of the steps described. To the contrary, the present descriptions are intended to cover such alternatives, modifications, and equivalents as may be included within the spirit and scope of the technology as defined by the appended claims and otherwise appreciated by one of ordinary skill in the art.

What is claimed is:

1. A medical glove, comprising: a cuff having an opening for hand entry and an opening edge; a body section coupled to the cuff; a plurality of finger members coupled to the body section generally opposite from the cuff, each finger member comprising a base end where the finger member is coupled to the body section and a tip end opposite the base end; a first channel integrally formed in the glove, the first channel comprising: a first open end proximate to the opening edge; a second open end proximate to the tip end of one of the finger members; and an enclosed hollow space connecting the first open end and the second open end wherein the second open end comprises a plurality of orifices.

2. The medical glove of claim 1, wherein the second open end extends at least partially around the tip end of the finger member.

3. The medical glove of claim 1, wherein the glove further comprises a first material that forms the channel.

4. The medical glove of claim 1, wherein each of the plurality of orifices has generally the same shape.

5. The medical glove of claim 1, wherein at least one of the plurality of orifices has a different shape or size than the other orifices.

6. The medical glove of claim 1, wherein at least a portion of the orifices are arranged in two or more rows.

7. The medical glove of claim 1, further comprising a second channel.

8. The medical glove of claim 7, wherein the second channel is positioned on the same finger member as the first channel.

9. The medical glove of claim 7, wherein the second channel is positioned on a different finger member than the first channel.

10. The medical glove of claim 7, wherein the first channel provides suction and the second channel provides irrigation.

11. The medical glove of claim 1, wherein the glove further comprises a first material and the channel is formed in a second material.

12. The medical glove of claim 1, further comprising one or more supporting structures to prevent collapse of the first channel when the first channel is under suction.

13. The medical glove of claim 1, wherein the first channel further comprises a tube embedded into the glove.

14. A medical glove, comprising: a cuff having an opening for hand entry and an opening edge; a body section coupled to the cuff; a plurality of finger members coupled to the body section generally opposite from the cuff, each finger member comprising a base end where the finger member is coupled to the body section and a tip end opposite the base end; a first channel integrally formed in the glove, the first channel comprising: a first open end proximate to the opening edge; a second open end proximate to the tip end of one of the finger members, the second open end comprising a plurality of orifices dispersed radially around at least a portion of the tip end of the finger member; and an enclosed hollow space connecting the first open end and the second open end.

15. The medical glove of claim 14, wherein each of the plurality of orifices has generally the same shape.

16. The medical glove of claim 14, wherein at least one of the plurality of orifices has a different shape or size than the other orifices.

17. The medical glove of claim 14, wherein at least a portion of the orifices are arranged in two or more rows.

18. The medical glove of claim 14, further comprising a second channel.

19. The medical glove of claim 18, wherein the second channel is positioned on the same finger member as the first channel.

20. The medical glove of claim 18, wherein the second channel is positioned on a different finger member than the first channel.

21. The medical glove of claim 18, wherein the first channel provides suction and the second channel provides irrigation.

22. The medical glove of claim 14, wherein the glove further comprises a first material and the channel is formed in a second material.

23. The medical glove of claim 14, further comprising one or more supporting structures to prevent collapse of the first channel when the first channel is under suction.

24. The medical glove of claim 14, wherein the channel further comprises a tube embedded into the glove.

25. A medical glove, comprising: a cuff having an opening for hand entry and an opening edge; a body section coupled to the cuff; a plurality of finger members coupled to the body section generally opposite from the cuff, each finger member comprising a base end where the finger member is coupled to the body section and a tip end opposite the base end; a channel integrally formed in the glove, the channel comprising: a first open end proximate to the opening edge; a second open end proximate to the tip end of one of the finger members; an enclosed hollow space connecting the first open end and the second open end; and a support member positioned within the channel and extending along at least a portion of a length of the channel, the support member having a generally hollow interior to allow the passage of liquids and gases through the channel, wherein the second open end comprises a plurality of orifices.

26. The medical glove of claim 25, wherein the second open end extends at least partially around the tip end of the finger member.

27. The medical glove of claim 25, wherein the glove further comprises a first material that forms the channel.

28. The medical glove of claim 25, further comprising a second channel.

29. The medical glove of claim 28, wherein the second channel is positioned on the same finger member as the first channel.

30. The medical glove of claim 28, wherein the second channel is positioned on a different finger member than the first channel.

31. The medical glove of claim 28, wherein the first channel provides suction and the second channel provides irrigation.

32. The medical glove of claim 25, wherein the glove further comprises a first material and the channel is formed in a second material.

33. The medical glove of claim 25, wherein the support member further comprises a tube.

34. A medical glove, comprising: a cuff having an opening for hand entry and an opening edge; a body section coupled to the cuff; a plurality of finger members coupled to the body section generally opposite from the cuff, each finger member comprising a base end where the finger member is coupled to the body section and a tip end opposite the base end; a channel integrally formed in the glove, the channel comprising: a first open end proximate to the opening edge; a second open end proximate to the tip end of one of the finger members; an enclosed hollow space connecting the first open end and the second open end; and a suction head inserted into the second open end, the suction head comprising a nipple that is at least partially inserted into the channel through the second open end, and a suction head extending outside the channel and generally conforming to a rounded shape of the tip end of the finger member, and a plurality of orifices dispersed along the suction head.

35. The medical glove of claim 34, wherein each of the plurality of orifices has generally the same shape.

36. The medical glove of claim 34, wherein at least one of the plurality of orifices has a different shape or size than the other orifices.

37. The medical glove of claim 34, wherein at least a portion of the orifices are arranged in two or more rows.

38. The medical glove of claim 34, wherein the glove further comprises first material and the channel is formed in a second material.

* * * * *